US00PP10694P

United States Patent [19]

Mak

[11] Patent Number: Plant 10,694

[45] Date of Patent: Nov. 17, 1998

[54] ORIENTAL HYBRID LILY PLANT NAMED 'WILDCARD'

[76] Inventor: Johan A. Mak, 5595 Halls Ferry Rd., Independence, Oreg. 97351

[21] Appl. No.: 918,894

[22] Filed: Aug. 27, 1997

[51] Int. Cl.[6] ..... A01H 5/00

[52] U.S. Cl. ..... Plt./87.4

[58] Field of Search ..... Plt./87.4

*Primary Examiner*—Howard J. Locker

[57] ABSTRACT

A new variety of hybrid lily plant bearing large flowers of excellent form and long persistence, both on the plant and as cut-flowers. The flowers of the new plant are particularly characterized by their white coloration with a soft yellow flame extending from the nectary furrows and red purple tepal spottings at the base of each tepal.

This combination is completely new in the Oriental hybrid divisions of lilies suited to forcing and to mass commercial cultivation. The variety is highly resistant to fusarium and botrytis disease. The bulbs may be precooled and forced for cut-flow production. The clone is vigorous and is a good grower and propagator.

1 Drawing Sheet

BACKGROUND OF THE INVENTION

My new variety of lily plant originated as a seedling which first flowered in't Zand, Netherlands, in 1988. The breeding efforts had as their objective the production of large-flowered Oriental hybrids in bicolored combinations of white with a yellow band and/or flame, suited to forcing into flower out of season, heretofore unknown in the lily breeding art.

I achieved the desired objective by intercrossing selected white Oriental seedlings, suited to forcing for year-round use as cut-flowers and carrying the recessive gene for a yellow flame.

The flowers of my new lily are characterized by large size and broad-tepalled form, with inner tepals overlapping slightly, by unusually thick substance, by white coloration with a small yellow flame extending 4 to 10 cm along the midrib from the nectaries of each tepal, and by red purple tepal spottings which is unique among Oriental hybrid lilies. It possesses unusually strong, stout stems. In addition, the clone possesses to a high degree desirable characteristics of hybrid vigor. The clone is a good grower and propagator, as observed at 't Zand, Netherlands, and at Salem, Oreg.

My new variety of lily plant has been asexually reproduced by me and under my direction at 't Zand, Netherlands, and at Salem, Oreg. Successive generations produced by natural propagation from bulblets, by bulb scale propagation, and by tissue culturing from bulb scale explants have demonstrated that the novel and distinctive characteristics of my new variety are fixed and hold true under asexual propagation from generation to generation.

DESCRIPTION OF THE DRAWING

My new variety of lily plant is illustrated in the accompanying photographic drawing, which shows the color of the bud, the open bloom in full color and illustrates the broad-tepalled flower form, the tepal arrangement, and in particular the novel and distinctive white flower with red purple spottings with a small yellow flame extending from the nectaries of each tepal.

DESCRIPTION OF THE NEW VARIETY

The following is a detailed description of my new variety of Oriental hybrid lily, with nomenclature according to the *International Lily Register* (Royal Horticultural Society of London, Second Edition, 1969), and with color designations according to the Color Chart of The Royal Horticultural Society, published by the Society in 1996.

The Plant

Origin: Seedling.

*Seed parent.*—Selected unnamed Oriental hybrid seedling.

*Pollen parent.*—Selected unnamed Oriental hybrid seedling.

Commercial classification: Hybrid Lilium clone.

Horticultural classification: Division VII-B, bowl-shaped Oriental hybrid lily, according to the Horticultural Classification of Lilies, Royal Horticultural Society of London.

Form: Single stem, erect and stately.

Height: 80 to 125 cm from bulbs 14 to 18 cm in circumference, provided light levels are adequate; low light levels may cause "stretching."

Growth: Vigorous and upright.

Foliage quantity: Abundant.

Size of leaf: Unusually broad, 2.5 to 4.5 cm wide ×13 to 16 cm long.

Shape of leaf: Lanceolate (pointed).

Texture: Leathery and glossy.

Color: Medium green R.H.S. C.C. 138 A-B, lighter on lower side.

Bulb:

*Size.*—Any size, ranging to 25 cm circumference commercially.

*Color.*—White, with flushes of pink or yellow after exposure to light.

The Bud

Form: Obtuse, ovoid, and long.

Size: 9 to 12 cm long and 8 to 12 cm in circumference just prior to opening.

Opening: Bud opens slowly, in response to morning light; this takes about one hour.

Color: Ivory white with pale green midribs.

Peduncle: Averages 5 to 7 cm, but it may elongate if light levels are too low or if bulbs have been improperly stored prior to forcing. Color is medium green with very light plum overlay.

The Flower

Blooming habit: Annually in midseason; flowers once and profusely.

Size: Flowers are large-sized, averaging 17.5 to 22 cm in diameter, reflexing at the tips on the second day to 15 to 19 cm in diameter. The tepals are broad: outer tepals are 2.75 to 3.75 cm wide, and the inner tepals are 4.5 to 6.5 cm wide and overlap at the base.

Borne: In a single racemic inflorescence producing 5 to 6 flowers from a bulb 14 to 16 cm in circumference.

Shape: Form a broad bowl shape by the second day after opening.

Tepalage: Typical of genus Lilium, with 6 imbricated tepals.

Tepal:

*Color.*—White with a yellow flame (R.H.S. C.C. Yellow 2D). The yellow color is slightly affected by temperatue and light levels; it decreases with high temperatures and low light levels. Tepal spotting: Red Purple R.H.S. C.C. 60B-C.

*Longevity.*—Tepals stay on stems about three weeks.

Pedicel:

*Length.*—Average 6 to 12 cm long.

*Color.*—Medium green (R.H.S. C.C. 143B) with very light plum overlay.

*Form.*—Sturdy and ascending.

Appearance: Flower is shiny.

Disease resistance: The flower and plant are resistant to disease; in particular, they are resistant to Fusarium bulb rot and Botrytis blight.

Frangrance: Light sweet fragrance.

Lasting quality: The flower is long lasting, both on the plant and as a cut-flower.

The Reproductive Organs

Stamens: Arrangement typical of genus Lilium. Six stamens with soft green to white filaments 7 to 9 cm long.

Pollen and anthers (dehisced): Greyed Orange R.H.S. C.C. 169A.

Pistil: One in number, 8 to 10 cm long.

Stigma: Red purple close to R.H.S. C.C. 60C, large in size.

Characteristics of ovary: Characteristic of genus Lilium.

The Fruit

Fertility: The fruit bears fertile seed.

Shape: Ovoid.

Color at maturity: Soft brown, sometimes overlaid with soft plum.

My new variety of Oriental hybrid lily most nearly resembles Lilium 'Casa Blanca', but it has a yellow flame and red purple spots. It also has outfacing or semi-upright flowers.

I claim:

1. A new and distinctive variety of Oriental hybrid lily plant substantially as herein shown and described, characterized by its high resistance to disease; its vigorous growth and rapid natural propagation; the excellence of its flower form, size, and substance; its versatility both as a garden plant and as a cut-flower producer from pre-cooled bulbs forced under glass out of season; and in particular by its broad-tepalled white flowers with a soft yellow flame extending from the nectary furrows and its red purple tepal spottings at the base of each tepal, a combination unique among Oriental hybrid lilies suited to forcing and to mass commercial cultivation.

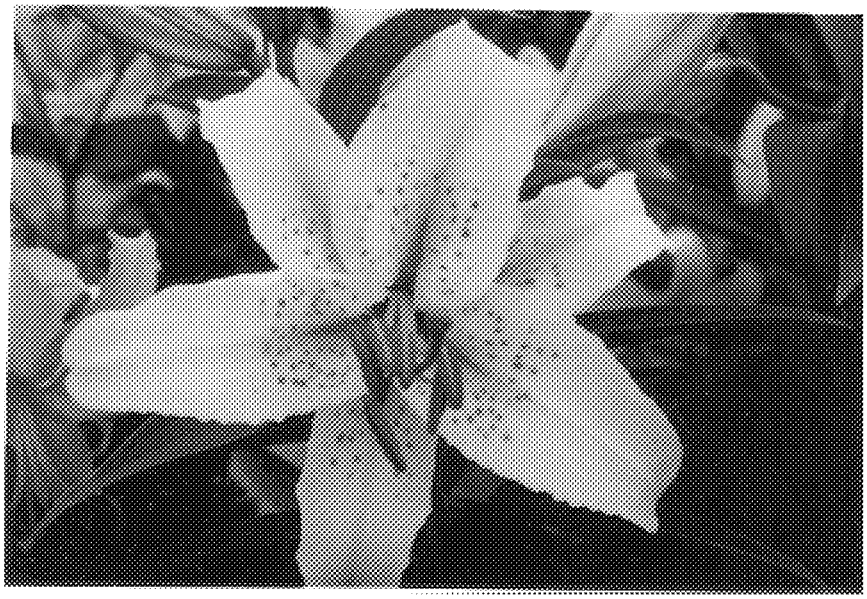

* * * * *